(12) United States Patent
Chang et al.

(10) Patent No.: US 12,715,824 B2
(45) Date of Patent: Aug. 25, 2026

(54) PLASMA CARBON SEQUESTRATION SYSTEM AND METHOD

(71) Applicant: XI'AN JIAOTONG UNIVERSITY, Xi'an (CN)

(72) Inventors: Zhengshi Chang, Xi'an (CN); Cong Wang, Xi'an (CN); Guanjun Zhang, Xi'an (CN)

(73) Assignee: XI'AN JIAOTONG UNIVERSITY, Xi'an (CN)

( * ) Notice: Subject to any disclaimer, the term of this patent is extended or adjusted under 35 U.S.C. 154(b) by 1062 days.

(21) Appl. No.: 17/864,089

(22) Filed: Jul. 13, 2022

(65) Prior Publication Data

US 2022/0340499 A1 Oct. 27, 2022

Related U.S. Application Data

(63) Continuation of application No. PCT/CN2020/079965, filed on Mar. 18, 2020.

(30) Foreign Application Priority Data

Jan. 17, 2020 (CN) ......................... 202010057594.5

(51) Int. Cl.
*C07C 1/12* (2006.01)
*B01J 19/08* (2006.01)
*C07C 31/04* (2006.01)

(52) U.S. Cl.
CPC ............... *C07C 1/12* (2013.01); *B01J 19/088* (2013.01); *C07C 31/04* (2013.01); (Continued)

(58) Field of Classification Search
CPC ......... C07C 1/12; C07C 31/04; B01J 19/088; B01J 2219/0013; B01J 2219/00759; (Continued)

(56) References Cited

U.S. PATENT DOCUMENTS 5,427,747 A 6/1995 Kong et al.
2016/0354754 A1* 12/2016 Hirson ..................... H05H 1/44
2019/0055655 A1* 2/2019 Xia ..................... B01D 5/0057

FOREIGN PATENT DOCUMENTS

CN 101550055 A 10/2009
CN 102612549 A 7/2012
(Continued)

OTHER PUBLICATIONS

International Search Report of PCT/CN2020/079965.
Written Opinion of PCT/CN2020/079965.

*Primary Examiner* — Xiuyu Tai

(57) ABSTRACT

A plasma carbon sequestration system and method are disclosed, wherein in the plasma carbon sequestration system, a first channel and a second channel of a plasma reactor are each provided with a flow controller, the plasma reactor is connected to a high voltage via a high voltage electrode and grounded via a ground electrode, water, or hydrogen, or methane is mixed with carbon dioxide respectively, to be introduced into the plasma reactor in a predetermined proportion under the control of the flow controllers, and a condenser is connected to the plasma reactor to condense a conversion product, and reactants which are not completely reacted from the plasma reactor, and is selectively used for circulation in the plasma reactor, thereby realizing environment-friendly treatment without a catalyst by a room temperature plasma technology.

7 Claims, 1 Drawing Sheet

(52) U.S. Cl.
CPC .................. *B01J 2219/0013* (2013.01); *B01J 2219/00759* (2013.01); *B01J 2219/0894* (2013.01)

(58) Field of Classification Search
CPC ........ B01J 2219/0894; B01J 2219/0869; B01J 2257/30; B01J 2219/0841; B01J 2219/0875; B01J 2219/0839; B01J 2219/0807; B01J 2219/0883; B01J 2219/0871; B01J 2219/0892; B01J 19/126; H05H 1/44; H05H 1/3484; C01B 2203/1241; C01B 3/38; C01B 3/342; C01B 3/384; C01B 2203/0844; C01B 2203/0238; C01B 2203/0861; C01B 2203/0811; C01B 2203/142; C01B 3/48; C01B 3/56; C01B 3/12; C01B 3/50; C01B 3/52; C01B 2203/86; C01B 2203/0827; C01B 2203/0233; C01B 2203/047; C01B 2203/043; C01B 2203/146; C01B 2203/0415; C01B 2203/062; C01B 2203/0283; C01B 2203/148; C01B 2203/0475; C01B 2203/04; C01B 2203/1258; C10J 2300/1659; C10J 2300/1681; C10J 2300/1665; C10J 2300/1238; C10J 2300/0946; C10J 2300/0969; C10J 2300/0916; C10J 2300/1815; C10J 2300/1668; C10J 3/18; C10J 2300/16; C10L 1/04; C10K 1/005; C10G 2/30; C10G 2300/1003; C10G 2300/1014; C10G 2300/4043; C10G 2300/405; C10G 2300/807; B01D 2257/2045; B01D 53/04
See application file for complete search history.

(56) References Cited

FOREIGN PATENT DOCUMENTS

| | | | |
|---|---|---|---|
| CN | 103143247 | A | 6/2013 |
| CN | 103796751 | A | 5/2014 |
| CN | 109200969 | A | 1/2019 |

* cited by examiner

PLASMA CARBON SEQUESTRATION SYSTEM AND METHOD

CROSS-REFERENCE TO RELATED APPLICATIONS

This application is a bypass continuation application of PCT application no.: PCT/CN2020/079965. This application claims priorities from PCT Application PCT/CN2020/079965, filed Mar. 18, 2020, and from Chinese patent application 202010057594.5, filed Jan. 17, 2020, the contents of which are incorporated herein in the entirety by reference.

TECHNICAL FIELD

The invention relates to the technical field of carbon dioxide conversion, in particular to a plasma carbon sequestration system and method.

BACKGROUND

On one hand, climate warming and resource depletion are the global problems that need to be solved urgently. The inefficient abuse of fossil energy leads to the lack of fossil energy and the excessive emission of $CO_2$, which makes the concentration of $CO_2$ in the atmosphere significantly increase, and causes the global average temperature to rise. For example, volatile organic compounds (VOCs) is a major source of air pollution, and long-term exposure to VOCs is also harmful to human health.

On the other hand, it is of great practical significance to capture and collect industrial waste gas and $CO_2$ resources in the atmosphere to be converted into fuel for storage by a certain technical means for improving the present situation of fossil energy and reducing atmospheric $CO_2$ concentration.

A molecular structure of $CO_2$ is very stable, and its high chemical inertness makes it difficult to activate. $CO_2$ is usually decomposed under the catalysis at high temperature, and the thermal energy cost is high. However, a process of $CO_2$ hydrofuelling is an exothermic reaction, and a high temperature is not conducive to the reaction.

At present, in the prior arts of $CO_2$ conversion and utilization, there are mainly the following problems:

1) most of the prior arts aim at realizing the synchronous resource utilization of $CO_2$ and $CH_4$, that is, a mixed gas of $CO_2$ and $CH_4$ is treated simultaneously, which is reformed into syngas containing CO and $H_2$ under certain conditions, and the syngas is further processed into chemical products as raw materials. However, the current technology leads to high reforming reaction temperature, low conversion efficiency, and serious carbon deposition, and the industrial application stage is not reached.
2) Under certain conditions, $CO_2$ can be directly converted to fuel through hydrogenation, which become a research hotspot at present, The existing $CO_2$ hydrogenation reaction systems mostly use catalysts, focusing on improving a catalyst structure, improving a catalyst synthesis method, synthesizing a new high-efficiency catalyst and optimizing reaction conditions, although $CO_2$ conversion efficiency is improved and a conversion product tends to be controllable, catalyst deactivation and catalyst secondary treatment have not been solved effectively.

The above information disclosed in the Background section is merely intended to enhance an understanding of the background of the present invention, and thus may contain information that does not constitute the prior art known to those of ordinary skill in the art.

SUMMARY

In order to solve the above problems, the present invention provides a plasma carbon sequestration system and method, which realize reforming of $CO_2$ and $CH_4$ or hydrofueling of $CO_2$ at room temperature by using a plasma technology, and reduce the energy consumption of a reaction. Different reactants are converted into different products in a plasma reactor. Fuel separation is realized by condensing and separating the products, and the separated substances can be recycled for reaction.

The object of the invention is achieved by the following technical solution.

A plasma carbon sequestration system, including, a plasma reactor, a first separator, a condenser, and a second separator; wherein the plasma reactor includes a first channel, a second channel, a high voltage electrode, and a ground electrode, and is connected to a high voltage via the high voltage electrode and is grounded via the ground electrode; wherein the first channel and the second channel are each provided with a corresponding flow controller; carbon dioxide is input into the plasma reactor via the first channel to be used as a first reactant, and hydrogen or methane or water is input into the plasma reactor via the second channel to be used as a second reactant, and the plasma reactor is configured to react the first reactant with the second reactant under the action of plasma and under the control of the flow controllers to obtain a conversion product, and the conversion product, and the first reactant and/or second reactant which may not be completely reacted are output to the condenser; the condenser is connected to an output of the plasma reactor, to ensure that under the condition that carbon dioxide which may not be completely reacted, hydrogen in the possibly obtained conversion product, and hydrogen which may not be completely reacted are not condensed, all conversion products from the plasma reactor, and methane or water which may not be completely reacted are condensed to achieve gas-liquid separation; and a liquid substance obtained by condensing is introduced into the first separator from the condenser, and the part of a gaseous substance that is not condensed is introduced into the second separator from the condenser, wherein the the part of the gaseous substance that is not condensed includes: carbon dioxide which may not be completely reacted, hydrogen in the possibly obtained conversion product, and hydrogen which may not be completely reacted; the condensed liquid substance from the condenser is separated one by one through the first separator, the separated fuel and chemical feedstock are stored for later use, and if necessary, the part of methane or water available for the second reactant is circulated to the plasma reactor via the second channel; and the part of the gaseous substance that is not condensed from the condenser is separated into carbon dioxide and other gases through the second separator, and the carbon dioxide is circulated to the plasma reactor via the first channel and the other gases are circulated to the plasma reactor via the second channel, wherein the other gases include the hydrogen in the possibly obtained conversion product and the hydrogen which may not be completely reacted.

According to another aspect of the invention, a carbon sequestration method of the plasma carbon sequestration system includes the following steps of, S100, with carbon dioxide as a first reactant, and hydrogen or methane or water as a second reactant, reacting the first reactant with the second reactant under the action of plasma and under the control of the reaction amount of the first reactant and the reaction amount of the second reactant to obtain a conversion product, and outputting and condensing the conversion product, and the first reactant and/or second reactant which may not be completely reacted to achieve gas-liquid separation; wherein, under the condition of ensuring that carbon dioxide which may not be completely reacted, hydrogen in the possibly obtained conversion product, and hydrogen which may not be completely reacted are not condensed, the conversion product, and methane or water which may not be completely reacted are condensed to achieve gas-liquid separation; S200, performing first separation on a liquid substance obtained by condensing, storing the separated fuel and chemical feedstock for later use, and if necessary, iterating the part of methane or water available for the second reactant again to the step S100 as the second reactant; and S300, performing second separation on the part of a gaseous substance that is not condensed, and iterating carbon dioxide available for the first reactant again to the step S100 as the first reactant, and iterating hydrogen available for the second reactant again to the step S100 as the second reactant.

Compared with the prior art, the beneficial effects of the present invention are: in the present invention, by utilizing plasma carbon sequestration without selectivity to reactants, a reforming reaction of $CO_2$ and $CH_4$ (i.e., carbon dioxide and methane), or a hydrogenation reaction of $CO_2$ and $H_2$ (i.e., carbon dioxide and hydrogen), $CO_2$ and $H_2O$ (i.e., carbon dioxide and hydrogen) can be realized. Since there is no need for a catalyst, the present invention can solve the problems caused by the use of a catalyst in $CO_2$ conversion at present, such as avoiding the problem of carbon deposition and deactivation of the catalyst; in addition, the present invention utilizes plasma carbon sequestration, which makes it possible to be carried out at room temperature, and solves the problem of temperature requirements for $CO_2$ decomposition and hydroconversion in the prior art, thereby greatly reducing the reaction temperature and avoiding the consumption of a large amount of thermal energy.

In other words, the plasma-based carbon sequestration technology disclosed in the present invention can efficiently reduce $CO_2$ and effectively utilize $CO_2$, and is a high-tech means of energy saving and emission reduction, which will greatly reduce carbon emissions and improve environmental quality.

The above description is only an overview of the technical solution of the present invention. In order to make the technical means of the invention more clearly understood, to the extent that those skilled in the art can implement the technical means according to the contents of the description, and to make the above and other objects, features and advantages of the invention more obvious and easy to understand, examples of specific embodiments of the present invention are given below.

BRIEF DESCRIPTION OF THE DRAWINGS

Various other advantages and benefits of the present invention will become apparent to those of ordinary skill in the art by reading the detailed description in the preferred embodiments below. The drawings are for the purpose of illustrating preferred embodiments only and are not to be considered to be a limitation of the invention. Obviously, the drawings described below are merely some embodiments of the present invention, and other drawings may be obtained from these drawings without inventive effort by one of ordinary skill in the art. Moreover, throughout the drawings, same reference signs denote same components.

In the drawings.

Figure 1:
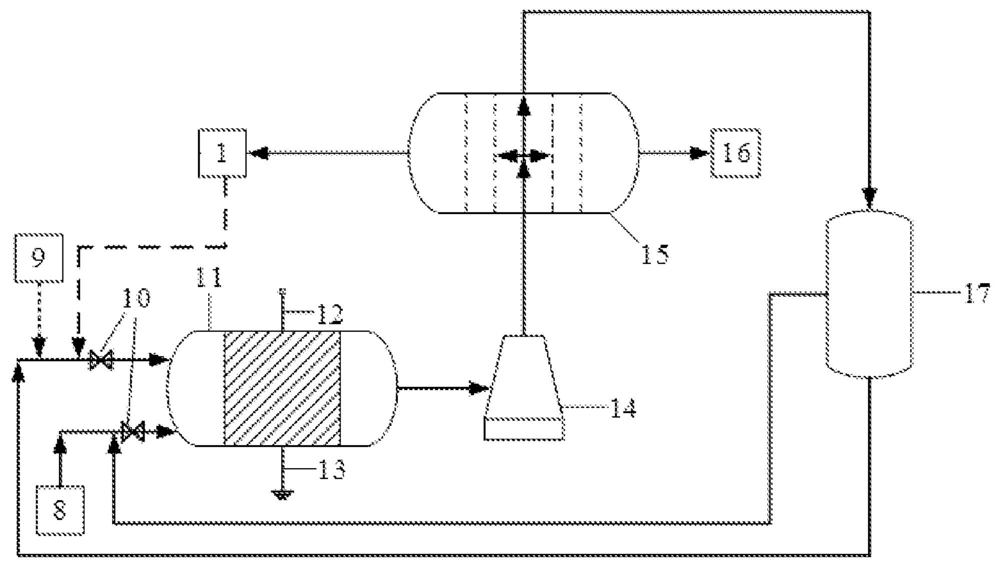
FIG. 1 is a structural schematic diagram of a plasma carbon sequestration system in one embodiment of the present invention.

The invention is further explained below with reference to the drawings and embodiments.

DETAILED DESCRIPTION

Specific embodiments of the present invention will be described in more detail below with reference to FIGS. 1-2. While specific embodiments of the invention have been shown in the drawings, it should be understood that the invention may be implemented in various forms and should not be limited by the embodiments set forth herein. On the contrary, these embodiments are provided so that the invention can be more fully understood, and the scope of the invention can be fully conveyed to those skilled in the art.

It should be noted that certain terms are used in the description and claims to refer to particular components. It should be understandable by those skilled in the art that those skilled may use different terms to refer to a same component. The present description and claims do not use differences in terms of terms as a means of distinguishing components, but rather use differences in the functions of components as a criterion of distinguishing. As used throughout the description and the claims, "including" or "comprising" is an open-ended term and is to be interpreted as "including but not limited to". The following description of the description is preferred embodiments of the invention, however, the description is for the purpose of the general principles of the description, but is not intended to limit the scope of the invention. The protection scope of the invention is defined by the appended claims.

To facilitate the understanding of embodiments of the present invention, further explanation will be given below with reference to the accompanying drawings by taking specific embodiments as examples, and the drawings do not constitute a limitation on the embodiments of the present invention.

For better understanding, as shown in FIG. 1, a plasma carbon sequestration system includes a plasma reactor 11, a first separator 15, a condenser 14, and a second separator 17; wherein the plasma reactor includes a first channel, a second channel, a high voltage electrode 12, and a ground electrode 13, and is connected to a high voltage via the high voltage electrode and is grounded via the ground electrode; wherein the first channel and the second channel are each provided with a corresponding flow controller 10; carbon dioxide is input into the plasma reactor 11 via the first channel to be used as a first reactant, and hydrogen or methane or water is input into the plasma reactor 11 via the second channel to be used as a second reactant, and the plasma reactor is configured to react the first reactant with the second reactant under the action of plasma and under the control of the flow controllers 10 to obtain a conversion product, and the conversion product, and the first reactant and/or second reactant which may not be completely reacted are output to the condenser 14; the condenser 14 is connected to an output of the plasma reactor, to ensure that under the condition that carbon dioxide which may not be completely reacted, hydrogen in the possibly obtained conversion product, and hydrogen which may not be completely reacted are not condensed, all conversion products from the plasma reactor, and methane or water which may not be completely reacted are condensed to achieve gas-liquid separation; and a liquid substance obtained by condensing is introduced into the first separator 15 from the condenser 14, and the part of a gaseous substance that is not condensed is introduced into the second separator 17 from the condenser 14, wherein the the part of the gaseous substance that is not condensed includes: carbon dioxide which may not be completely reacted, hydrogen in the possibly obtained conversion product, and hydrogen which may not be completely reacted; it should be noted that the existing condensers may ensure that: while the carbon dioxide which may not be completely reacted, the hydrogen in the possibly obtained conversion product, and the hydrogen which may not be completely reacted are not condensed, all conversion products from the plasma reactor, and the methane or water which may not be completely reacted are condensed to achieve gas-liquid separation, which can be selected in a wide range of models.

the condensed liquid substance from the condenser 14 is separated one by one through the first separator 15, the separated fuel and chemical feedstock are stored for later use, and if necessary, the part of methane or water available for the second reactant is circulated to the plasma reactor 11 via the second channel; the part of the gaseous substance that is not condensed from the condenser 14 is separated into carbon dioxide and other gases through the second separator 17, and the carbon dioxide is circulated to the plasma reactor 11 via the first channel and the other gases are circulated to the plasma reactor 11 via the second channel, wherein the other gases include the hydrogen in the possibly obtained conversion product and the hydrogen which may not be completely reacted.

It can be understood that this embodiment realizes the reforming of $CO_2$ and $CH_4$, and the hydroconversion of $CO_2$ at room temperature, which is of a great significance for achieving high-efficiency fueling of $CO_2$ and reducing energy loss. Typically, by making full use of excess distributed power energy, discharging under the action of high voltage produces plasma to activate $CO_2$ molecules at room temperature, and a mixed gas of $CO_2$ and $CH_4$, $CO_2$ and $H_2O$ or $CO_2$ and $H_2$ is introduced into the plasma reactor in a certain proportion to realize the fuel conversion of $CO_2$, so as to obtain new chemical fuels to be stored and utilized, to achieve high-efficiency carbon sequestration and to improve the environmental quality effectively, which is of a great practical significance for quickly achieving the goal of low carbon emission and realizing the application of $CO_2$ fueling.

For a further understanding of the present invention, as shown in FIG. 1, signs in the figure are: 1—$H_2O$; 8—$CO_2$; 9—$CH_4$; 16—CO, $CH_4$, $CH_3OH$, or $O_2$ and other conversion products, a reaction principle is detailed below:

1) under the action of plasma formed by a high voltage, $CO_2$ and $H_2$ can undergo the following conversion reaction:

$$CO_2+3H_2 \rightarrow CH_3OH+H_2O$$

after the above conversion reaction of $H_2$ and $CO_2$, $CH_3OH$ and $H_2O$ are generated, which are condensed by the condenser 14 and separated by the first separator to obtain $CH_3OH$ and $H_2O$, respectively. The separated $CH_3OH$ can be stored as a fuel for later use, while $H_2O$ can be recycled for reaction or used for ionization to obtain hydrogen and oxygen. If unreacted carbon dioxide or hydrogen is present, the carbon dioxide or hydrogen can be recycled.

It can be understood that for the above reaction, $H_2$ and $CO_2$ are preferably introduced into the plasma reactor 11 in a ratio of 3:1.

2) Under the action of the plasma formed by the high voltage, $CO_2$ and $H_2$ can undergo the following conversion reaction:

$$CO2+4H_2 \rightarrow CH_4+2H_2O$$

It can be understood that for the above reaction, $H_2$ and $CO_2$ are preferably introduced into the plasma reactor 11 in a ratio of 4:1. The products $CH_4$ and $H_2O$ are condensed by the condenser 14 and separated by the first separator to obtain $CH_4$ and $H_2O$, respectively. The separated $CH_4$ can be stored for later use or recycled for reaction (see a fourth reaction below), while $H_2O$ can be recycled for reaction or used for ionization to obtain hydrogen and oxygen. The unreacted carbon dioxide or hydrogen can be continued to be recycled.

3) Under the action of the plasma formed by the high voltage, $CO_2$ and $H_2$ can undergo the following conversion reaction:

$$CO_2+H_2 \rightarrow CO+H_2O$$

It can be understood that for the above reaction, $H_2$ and $CO_2$ are preferably introduced into the plasma reactor 11 in a ratio of 1:1. The products CO and $H_2O$ are condensed and separated to obtain separated CO and $H_2O$ respectively. The separated CO can be stored for standby application as raw materials for synthesis of other chemical products, while $H_2O$ can be recycled for reaction or used for ionization to obtain hydrogen and oxygen. The unreacted carbon dioxide or hydrogen can be continued to be recycled.

4) Under the action of the plasma formed by the high voltage, $CO_2$ and $CH_4$ can undergo the following conversion reaction:

$$CO_2+CH_4 \rightarrow 2CO+2H_2$$

It can be understood that for the above reaction, $CH_4$ and $CO_2$ are preferably introduced into the plasma reactor 11 in a ratio of 1:1. The products CO and $H_2$ are condensed and separated to obtain separated CO and $H_2$. The separated CO can be stored for standby application as raw materials for synthesis of other chemical products, while $H_2$ can be recycled for reaction or used for other purposes. The unreacted carbon dioxide or methane can be continued to be recycled.

5) Under the action of the plasma formed by the high voltage, $CO_2$ and $H_2O$ can undergo the following conversion reaction:

$$CO_2+2H_2O \rightarrow CH_4+2O_2$$

It can be understood that for the above reaction, $H_2O$ and $CO_2$ are preferably introduced into the plasma reactor 11 in a ratio of 2:1. The products $CH_4$ and $O_2$ are condensed and separated to obtain separated $CH_4$ and $O_2$ respectively. The separated $O_2$ can be stored for standby application or discharged directly to the atmosphere, while $CH_4$ can be recycled for reaction or used for other purposes. The unreacted carbon dioxide or water can be continued to be recycled.

It should be noted that the carbon dioxide participating in the reaction may be from industrial waste gas or atmospheric capture, which may be used in the prior art. The substances on the right side of the above reactions belong to the mainstream possible situation of all conversion products, this is because, in the plasma reactor, although the present invention can control an initial ratio through the above flow controllers and the above reactions, since the reaction conditions in the plasma reactor cannot be precisely controlled, although the mainstream products are methanol, methane, carbon monoxide, water, oxygen, hydrogen, etc., it is not excluded to obtain other hydrocarbons or alcohols, such as ethane, ethanol, etc. As for the second reactant according to the present invention, i.e. water or hydrogen or methane, there are also a variety of sources of access, whether purchased separately or obtained by other means.

In another embodiment, such reactants as carbon dioxide and/or water may also preferably be from VOCs, and typically the system further includes: a volatile organic compound (VOC) degradation system 5, configured to generate a degradation product containing carbon dioxide and water, and a third separator 4, connected to the degradation system 5 to separate carbon dioxide and water from the degradation product; in combination with the foregoing, the carbon dioxide, and water can be used directly as reactants to perform carbon sequestration in accordance with the reaction described in 5).

It can be understood that it is the proper meaning of the invention to participate in the conversion reaction of the above-described carbon sequestration system by collecting $CO_2$ in air or industrial waste gas or $CO_2$ obtained from the degradation of VOCs, so as to solve the problem of carbon emission in environmental protection to a certain extent. Moreover, $H_2O$ obtained from the degradation of VOCs can also participate in the carbon sequestration reaction.

Figure 2:
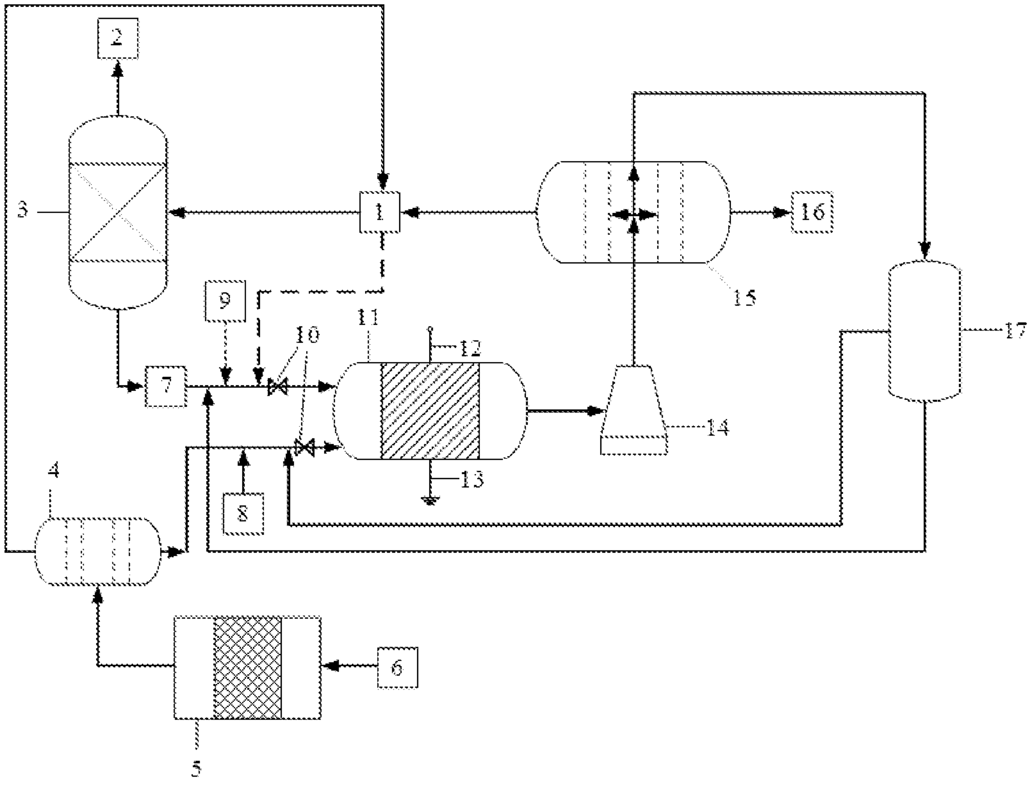
FIG. 2 is a structural schematic diagram of a plasma carbon sequestration system in another embodiment of the present invention.

In another embodiment, the water is further ionized, for a further understanding of the present invention, as shown in FIG. 2, signs in the figure are: 1—$H_2O$; 2—$O_2$; 6—VOCs; 7—$H_2$; 8—$CO_2$; 9—$CH_4$; 16—CO, $CH_4$, $CH_3OH$ and other conversion products: in combination with FIG. 2, the system may further include: a water ionization reactor 3 connected to the third separator 4 to ionize the water to produce oxygen and hydrogen; it can be understood that oxygen can be discharged directly to the atmosphere or spare, while hydrogen can be used directly as the first reactant described above, and carbon sequestration is performed with hydrogen and carbon dioxide according to the above-mentioned reaction formula; that is, in combination with the foregoing: water from the third separator 4, or hydrogen from the water ionization reactor 3, or methane from the first separator 15, and carbon dioxide can be introduced into the plasma reactor 11 in a predetermined ratio under the control of the flow controllers 10.

It can be understood that each of the above separators and reactors includes a certain interior space.

In another embodiment, the plasma reactor includes a structure for generating plasma by surface discharge, dielectric barrier discharge, pulse discharge, corona discharge, plasma jet, a packed bed reactor, are discharge, or gliding arc discharge.

In another embodiment, the high voltage is an alternating current voltage, a direct current voltage, a pulsed voltage, or any other waveform high voltage.

In another embodiment, the VOC degradation system degrades VOC gases to a degradation product containing carbon dioxide and water by using any one or any combination of the following techniques: catalysis, combustion, a plasma technology, biotechnology.

In another embodiment, the VOC degradation system is connected to industrial waste gases containing VOC gases.

More generally, because the reaction environment in the plasma reactor cannot be precisely controlled, in preferred embodiments of the plasma carbon sequestration system, the conversion product may include formaldehyde or other aldehydes or other carbon-containing compounds.

Further, in another embodiment, the present invention also discloses a plasma carbon sequestration method, including the following steps of, S100, with carbon dioxide as a first reactant, and hydrogen or methane or water as a second reactant, reacting the first reactant with the second reactant under the action of plasma and under the control of the reaction amount of the first reactant and the reaction amount of the second reactant to obtain a conversion product, and outputting and condensing the conversion product, and the first reactant and/or second reactant which may not be completely reacted to achieve gas-liquid separation; wherein, under the condition of ensuring that carbon dioxide which may not be completely reacted, hydrogen in the possibly obtained conversion product, and hydrogen which may not be completely reacted are not condensed, the conversion product, and methane or water which may not be completely reacted are condensed to achieve gas-liquid separation; S200, performing first separation on a liquid substance obtained by condensing, storing the separated fuel and chemical feedstock for later use, and if necessary, iterating the part of methane or water available for the second reactant again to the step S100 as the second reactant; and S300, performing second separation on the part of a gaseous substance that is not condensed, and iterating carbon dioxide available for the first reactant again to the step S100 as the first reactant, and iterating hydrogen available for the second reactant again to the step S100 as the second reactant.

According to the invention, the decomposition and conversion of $CO_2$ can be realized at normal temperature, $CO_2$ is converted into fuel or chemical feedstock, a large amount of heat energy is saved, reaction energy consumption is reduced, and there is no need for a catalyst, which has a practical engineering significance for realizing the treatment of $CO_2$.

INDUSTRIAL APPLICABILITY

The plasma carbon sequestration system and method provided by the invention can be manufactured and used in the field of carbon dioxide conversion.

While the basic principles of the present application have been described above in connection with specific embodiments, it should be noted that the virtues, advantages, effects, and the like mentioned in this application are merely exemplary and not restrictive, and that these virtues, advantages, effects, and the like are not to be considered essential to various embodiments of the present application. In addition, the specific details disclosed above are for purposes of illustration and easy understanding only, rather than limiting, and the above details are not intended to limit a fact that the present application must be implemented with the specific details described above.

The foregoing description has been presented for purposes of illustration and description.

Moreover, this description is not intended to limit the embodiments of the present application to the forms disclosed herein. While a number of example aspects and embodiments have been discussed above, those skilled in the art will recognize certain variations, modifications, alterations, additions, and subcombinations thereof.

The invention claimed is:

1. A plasma carbon sequestration system, comprising, a plasma reactor, a condenser, a first separator connected to and in fluid communication with the condenser, a second separator connected to and in fluid communication with the condenser, a third separator, a water ionization reactor and a volatile organic compound (VOC) degradation system; wherein the plasma reactor comprises a first channel, a second channel, a high voltage electrode, a ground electrode, and an outlet, and is connected to a high voltage via the high voltage electrode and is grounded via the ground electrode; wherein the first channel and the second channel are each provided with a corresponding flow controller;

the condenser is connected to and in fluid communication with and the outlet of the plasma reactor and is configured to condense a portion of substances output from the plasma reactor to form a condensed liquid and a non-condensed gas; the condensed liquid is introduced into the first separator from the condenser and the non-condensed gas from the condenser is separated through the second separator into carbon dioxide and a first hydrogen, the carbon dioxide being circulated to the plasma reactor via the first channel and the first hydrogen being circulated to the plasma reactor via the second channel;

the volatile organic compound (VOC) degradation system is configured to generate a degradation product containing carbon dioxide and water and to separate carbon dioxide and water;

the water separated by the third separator is directed through a conduit to the water ionization reactor;

the third separator is connected to and in fluid communication with an outlet of the VOC degradation system to separate carbon dioxide and water from the degradation product, and the water ionization reactor is connected to and in fluid communication with an outlet of the third separator and is configured to ionize the water separated by the third separator to produce oxygen and a second hydrogen, wherein the second hydrogen is introduced into the plasma reactor via the second channel and the oxygen is discharged.

2. The plasma carbon sequestration system according to claim 1, wherein the carbon dioxide is from industrial waste gas or captured and collected from the atmosphere, or from the volatile organic compound (VOC) degradation system.

3. The plasma carbon sequestration system according to claim 1, wherein, one of the following conversion modes is performed:

1) $H_2$ and $CO_2$ are mixed and introduced into the plasma reactor in a ratio of 3:1 under the control of the flow controllers to be converted into $CH_3OH$ and $H_2O$; or 2) $H_2$ and $CO_2$ are mixed and introduced into the plasma reactor in a ratio of 4:1 under the control of the flow controllers to be converted into $CH_4$ and $H_2O$; or 3) $H_2$ and $CO_2$ are mixed and introduced into the plasma reactor in a ratio of 1:1 under the control of the flow controllers to be converted into CO and $H_2O$; or 4) $CH_4$ and $CO_2$ are mixed and introduced into the plasma reactor in a ratio of 1:1 under the control of the flow controllers to be converted into CO and $H_2$; or 5) $H_2O$ and $CO_2$ are mixed and introduced into the plasma reactor in a ratio of 2:1 under the control of flow controllers to be converted into $CH_4$ and $O_2$.

4. The plasma carbon sequestration system according to claim 1, wherein the plasma reactor comprises a structure for generating plasma by surface discharge, dielectric barrier discharge, pulse discharge, corona discharge, plasma jet, a packed bed reactor, arc discharge, or gliding arc discharge.

5. The plasma carbon sequestration system according to claim 1, wherein the high voltage is an alternating current voltage, a direct current voltage, or a pulsed voltage.

6. The plasma carbon sequestration system according to claim 1, wherein the VOC degradation system degrades VOC gases to a degradation product containing carbon dioxide and water by using any one or any combination of the following techniques: catalysis, combustion, a plasma technology, and biotechnology.

7. The plasma carbon sequestration system according to claim 1, wherein the VOC degradation system is connected to industrial waste gas containing VOC gases.

* * * * *